United States Patent
Trotter et al.

(10) Patent No.: US 10,088,407 B2
(45) Date of Patent: Oct. 2, 2018

(54) SYSTEMS AND METHODS FOR EFFICIENT CONTOURS AND GATING IN FLOW CYTOMETRY

(71) Applicant: BECTON, DICKINSON AND COMPANY, Franklin Lakes, NJ (US)

(72) Inventors: Joseph Trotter, La Jolla, CA (US); Christopher Wolf, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 587 days.

(21) Appl. No.: 14/277,527

(22) Filed: May 14, 2014

(65) Prior Publication Data

US 2014/0343897 A1 Nov. 20, 2014

Related U.S. Application Data

(60) Provisional application No. 61/824,824, filed on May 17, 2013.

(51) Int. Cl.
| | |
|---|---|
| *G01N 15/14* | (2006.01) |
| *G06T 7/194* | (2017.01) |
| *G06T 7/12* | (2017.01) |
| *G06T 9/20* | (2006.01) |
| *G06K 9/00* | (2006.01) |
| *G06K 9/46* | (2006.01) |
| *G01N 15/10* | (2006.01) |

(52) U.S. Cl.
CPC ....... *G01N 15/1429* (2013.01); *G06K 9/0014* (2013.01); *G06K 9/4638* (2013.01); *G06T 7/12* (2017.01); *G06T 7/194* (2017.01); *G06T 9/20* (2013.01); *G01N 2015/1006* (2013.01); *G01N 2015/1402* (2013.01)

(58) Field of Classification Search
None
See application file for complete search history.

(56) References Cited

U.S. PATENT DOCUMENTS

| | | | |
|---|---|---|---|
| 4,845,653 A | 7/1989 | Conrad et al. |
| 4,976,035 A | 12/1990 | Levy et al. |
| 5,627,040 A | 5/1997 | Bierre et al. |
| 5,739,000 A | 4/1998 | Bierre et al. |
| 5,795,727 A | 8/1998 | Bierre et al. |
| 5,962,238 A | 10/1999 | Sizto et al. |
| 6,014,904 A | 1/2000 | Lock |

(Continued)

OTHER PUBLICATIONS

Walther et al., "Automatic Clustering of Flow Cytometry Data with Density-Based Merging" Hindawi Publishing Corporation Advances in Bioinformatics vol. 2009, Article ID 686759, 7 pages.*

(Continued)

*Primary Examiner* — John Kuan
(74) *Attorney, Agent, or Firm* — Knobbe Martens Olson & Bear LLP

(57) ABSTRACT

Methods and systems for efficient contour and gating in flow cytometry are provided. Event data is compressed to reduce the number of points needed to represent polygon contours for the event data. Selection of a level within the contour then causes the generation of a gate. This allows limited resource devices, such as touchscreen wireless devices, to render and gate flow cytometry data in a resource efficient manner.

20 Claims, 13 Drawing Sheets

(56) References Cited

U.S. PATENT DOCUMENTS

| | | |
|---|---|---|
| 6,944,338 B2 | 9/2005 | Lock et al. |
| 2007/0188491 A1 | 8/2007 | Denelsbeck et al. |
| 2008/0263468 A1* | 10/2008 | Cappione ......... G01N 35/00722 715/771 |
| 2012/0245889 A1 | 9/2012 | Zhu et al. |

OTHER PUBLICATIONS

Bauer et al. (eds.), Clinical Flow Cytometry: Principles and Applications, Williams & Wilkins (1993).

Jaroszeski et al. (eds.), Flow Cytometry Protocols, Methods in Molecular Biology No. 91, Humana Press (1997).

Landay et al. (eds.), Clinical Flow Cytometry, Annals of the New York Academy of Sciences vol. 677 (1993).

Ormerod (ed.), Flow Cytometry: A Practical Approach, Oxford Univ. Press (1997).

Pawley (ed.), Handbook of Biological Confocal Microscopy, 2nd Edition, Plenum Press (1989).

Shapiro, Practical Flow Cytometry, 4th ed., Wiley-Liss (2003).

Gregori, G et al. "Introduction to WinMDI 2.8 (J. Trotter 1993-1998) for the Analysis of Flow Cytometry Listmode Data Files" Publication [online]. Jul. 2003 [retrieved Aug. 8, 2014]. Retrieved from the Internet:URL:https://www.einstein.yu.edu/uploadedFiles/Facs/WinMDITutorial.pdf?n=2634; entire document.

Herzenberg, LA et al. "Interpreting flow cytometry data: a guide for the perplexed nature" Nature Immunology Jul. 2006, vol. 7, No. 7; pp. 681-685; entire document.

Wilshire, J. "FlowJo Basic Tutorial" Publication [online]. Mar. 2002, Version 1.1 [retrieved on Aug. 8, 2014]. Retrieved from the internet: <URL:http://www.imm.fm.ul.pt/wiki/lib/exe/fetch.php?media=facility:flowcyt:flowjo_basic_tutorial.pdf>; entire document.

International Search Report for International Application No. PCT/US14/38106 dated Sep. 15, 2014.

Supplementary European Search Report for Europe Application No. EP 14 79 7800 dated Dec. 9, 2016.

\* cited by examiner

Filling Contours

⊘ >= Contour Level

⊘ < Contour Level

Create a code for each case, and bits are assigned like this:

0  1
3  2

1111, Tile completely filled 0001, 1110
0010, 1101
0011, 1100
0100, 1011
0110, 1001
0111, 1000

0101, 1010, there are two possible configurations depending on the average of the center point

SYSTEMS AND METHODS FOR EFFICIENT CONTOURS AND GATING IN FLOW CYTOMETRY

CROSS-REFERENCE TO RELATED APPLICATIONS

This application claims a priority benefit under 35 U.S.C. § 119(e) from U.S. Provisional Patent Application No. 61/824,824, entitled "Systems and Methods for Efficient Contours and Gating in Flow Cytometry," filed May 17, 2013, which is incorporated by reference in its entirety. Any and all priority claims identified in the Application Data Sheet, or any correction thereto, are also hereby incorporated by reference under 37 C.F.R. § 1.57.

BACKGROUND

Technical Field

This disclosure relates to contours and gating of data, and in particular to efficient contours for gating and gate manipulations of cytometer data such as flow cytometer populations.

Background

Particle analyzers, such as flow and scanning cytometers, are analytical tools that enable the characterization of particles on the basis of optical parameters such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection. A multiplicity of different particles or components may be simultaneously detected by using spectrally distinct fluorescent dyes to label the different particles or components. In some implementations, a multiplicity of photodetectors, one for each of the scatter parameters to be measured, and one for each of the distinct dyes to be detected are included in the analyzer. The data obtained comprise the signals measured for each of the light scatter parameters and the fluorescence emissions.

Cytometers may further comprise means for recording the measured data and analyzing the data. For example, data storage and analysis may be carried out using a computer connected to the detection electronics. For example, the data can be stored in tabular form, where each row corresponds to data for one particle, and the columns correspond to each of the measured parameters. The use of standard file formats, such as an "FCS" file format, for storing data from a flow cytometer facilitates analyzing data using separate programs and/or machines. Using current analysis methods, the data typically are displayed in 2-dimensional (2D) plots for ease of visualization, but other methods may be used to visualize multidimensional data.

The parameters measured using a flow cytometer typically include the excitation light that is scattered by the particle along a mostly forward direction, referred to as forward scatter (FSC), the excitation light that is scattered by the particle in a mostly sideways direction, referred to as side scatter (SSC), and the light emitted from fluorescent molecules in one or more channels (range of frequencies) of the spectrum, referred to as FL1, FL2, etc., or by the fluorescent dye that is primarily detected in that channel. Different cell types can be identified by the scatter parameters and the fluorescence emissions resulting from labeling various cell proteins with dye-labeled antibodies.

Both flow and scanning cytometers are commercially available from, for example, BD Biosciences (San Jose, Calif.). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1994); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed.), Handbook of Biological Confocal Microscopy, 2nd Edition, Plenum Press (1989), incorporated herein by reference.

The data obtained from an analysis of cells (or other particles) by multi-color flow cytometry are multidimensional, wherein each cell corresponds to a point in a multi-dimensional space defined by the parameters measured. Populations of cells or particles are identified as clusters of points in the data space. The identification of clusters and, thereby, populations can be carried out manually by drawing a gate around a population displayed in one or more 2-dimensional plots, referred to as "scatter plots" or "dot plots," of the data. Alternatively, clusters can be identified, and gates that define the limits of the populations, can be determined automatically. Examples of methods for automated gating have been described in, for example, U.S. Pat. Nos. 4,845,653; 5,627,040; 5,739,000; 5,795,727; 5,962,238; 6,014,904; 6,944,338; and U.S. Pat. Pub. No. 2012/0245889, each incorporated herein by reference.

Gating is used to help make sense of the large quantity of data that may be generated from a sample. Accordingly, facilitating the creation and manipulation of gates efficient can help improve the speed and accuracy of understanding what the results mean.

SUMMARY

The systems, methods and devices of the disclosure each have several innovative aspects, no single one of which is solely responsible for the desirable attributes disclosed herein.

In one innovative aspect, a method for generating a contour, a tangible machine readable storage device having computer-executable instructions stored thereon for generating a contour, and a system for generating a contour are described with reference to the accompanying drawings.

For example, in one implementation, a method of generating a contour is described. The method includes obtaining an initial contour, the initial contour including a first plurality of points. The first plurality of points is indicative of event density within a set of flow cytometry data. The method further includes generating the contour based on the initial contour, the contour having a second plurality of points wherein the second plurality of points is less than the first plurality of points. In some implementations, the method also includes receiving a message including an identifier for a level of the contour and generating a gate based on the identified level of the contour.

In a further innovative aspect, a method for generating a gate; a tangible machine readable storage device having computer-executable instructions stored thereon for generating a gate; or a system for generating a gate substantially as hereinbefore described with reference to the accompanying drawings.

For example, in one innovative aspect, a method of generating a gate is provided. The method includes obtaining a contour for a set of data, the contour including one or more contour levels. The method also includes receiving a message, the message identifying a contour level of the one or more contour levels. The method further includes generating the gate for the set of data based on the identified contour level.

DETAILED DESCRIPTION

Figure 1:
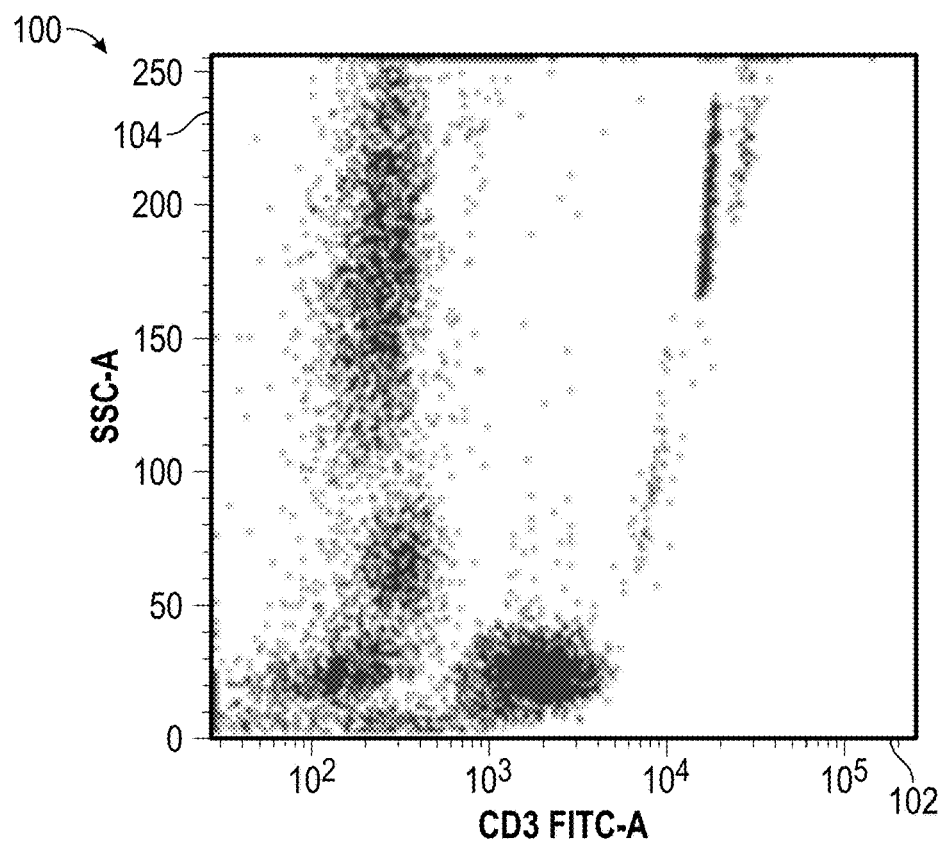
FIG. 1 shows an example of a dot-plot diagram.

The features described allow a user to quickly create a contour using a dot-plot graph in combination with a contour algorithm. The features may be implemented to efficiently generate information regarding a contour such that the information can be shown in the foreground, in real-time, as the user selects a portion of the graphic. In another implementation, the information may also include a classifier for a portion of the graph to facilitate graphical selection of an area via a touch screen device such as a tablet.

The generated contour may also be used to classify events within the data set. The contour may also provide an abstraction of those events for other purposes, such as generating new displays, conveying bitmap information or other forms of the data. The abstractions may be provided, for example, to firmware for subsequent processing, or to mobile devices for display. In some implementations, the abstractions may be stored for in a memory for future processing. The contour plot model generated by the described systems and methods may also be implemented as a transparent layer overlaid onto a second plot model/layer located underneath to enable selection of objects (populations) which can be rendered by the second visible layer below.

As used herein, "system" and "instrument" and "apparatus" generally encompass both the hardware (e.g., mechanical and electronic) and associated software (e.g., computer programs) components.

As used herein, an "event" generally refers to the data measured from a single particle, such as cells or synthetic particles). Typically, the data measured from a single particle are include a number of parameters, including one or more light scattering parameters, and at least one fluorescence intensity parameters. Thus, each event is represented as a vector of parameter measurements, wherein each measured parameter corresponds to one dimension of the data space.

As used herein, a "population", or "subpopulation" of particles, such as cells or other particles, generally refers to a group of particles that possess optical properties with respect to one or more measured parameters such that measured parameter data form a cluster in the data space. Thus, populations are recognized as clusters in the data. Conversely, each data cluster generally is interpreted as corresponding to a population, although clusters that correspond to noise or background typically also are observed. A cluster may be defined in a subset of the dimensions, e.g., with respect to a subset of the measured parameters, which corresponds to populations that differ in only a subset of the measured parameters.

As used herein, a "gate" generally refers to a set of boundary points identifying a subset of data of interest. In cytometry, a gate may bound a group of events of particular interest. As used herein, "gating" generally refers to the process of defining a gate for a given set of data.

As briefly discussed above, dot-plots are one way to visualize the data produced by the cytometer. When displaying and analyzing data, histogram, 2D density, and/or contour plots may also be used.

FIG. 1 shows an example of a dot-plot diagram. The dot-plot 100 displays a scatter plot of the events in an x-plane 102 and a y-plane 104. The x-plane 102 illustrates the parameter of interest. In the example shown in FIG. 1, the x-plane 102 represents light intensity for FITC-A CD3 antibodies. The y-plane 103 shows the side scatter count (SSC). The side scatter count may be referred to as events or event count.

The plot can be drawn such that several populations of data are identified. Each population may be represented using a unique color. An advantage of the dot-plot 100 is that populations can be readily distinguished from one another visually. This can be useful when comparing different data sets. One significant disadvantage of the dot-plot 100 is that the diagram does not include information about how dense the data is. In addition, the dot-plot 100 can get saturated when there are hundreds of thousands of events. This may lead to a loss of fidelity of clusters which may be co-located or closely located. To help provide density information, one or more of the other plot types may be used.

Figure 2:
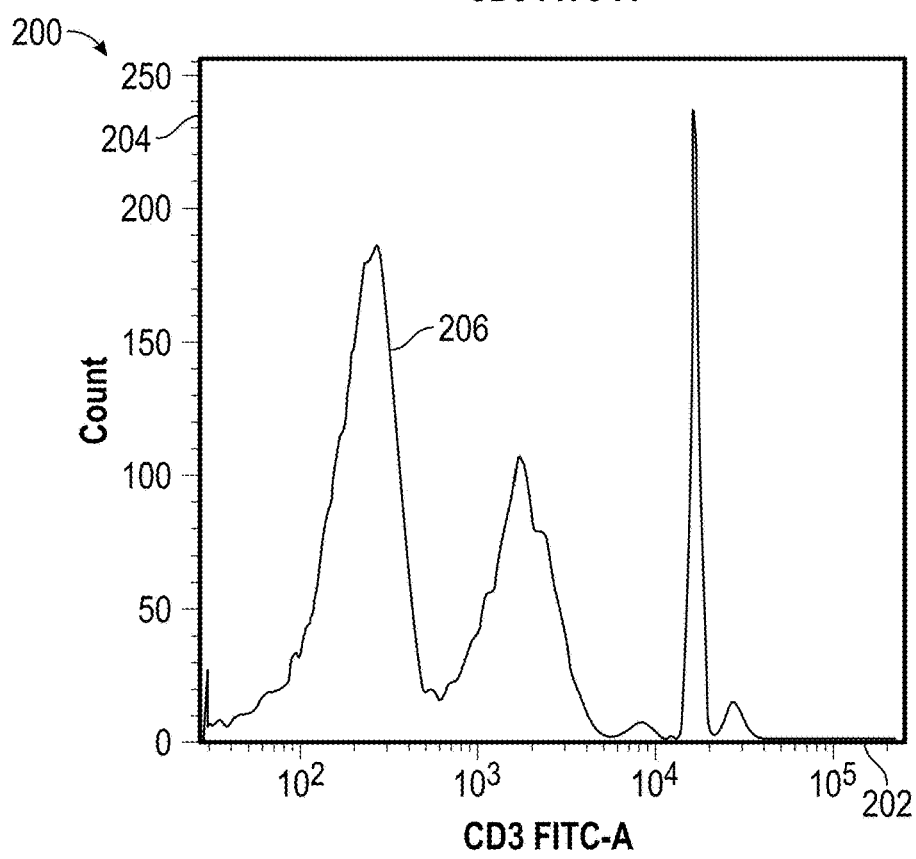
FIG. 2 shows an example of a histogram plot diagram.

FIG. 2 shows an example of a histogram plot diagram. The histogram plot diagram 200 shows data density for a given parameter. In the example shown in FIG. 2, the histogram plot diagram 200 plots along an x-axis 202 the parameter of interest and along a y-axis 204 the count for each parameter. A line 206 can be drawn, connecting the counts at some or all of the parameters. The peaks and valleys provide information about the relative density of events for given parameters. Thus, the histogram plot diagram 200 provides a visual representation of the density of the data, that is, how many occurrences of an event happened at a particular parameter. One limitation of the histogram plot diagram is that it shows density of the data in one direction.

Figure 3:
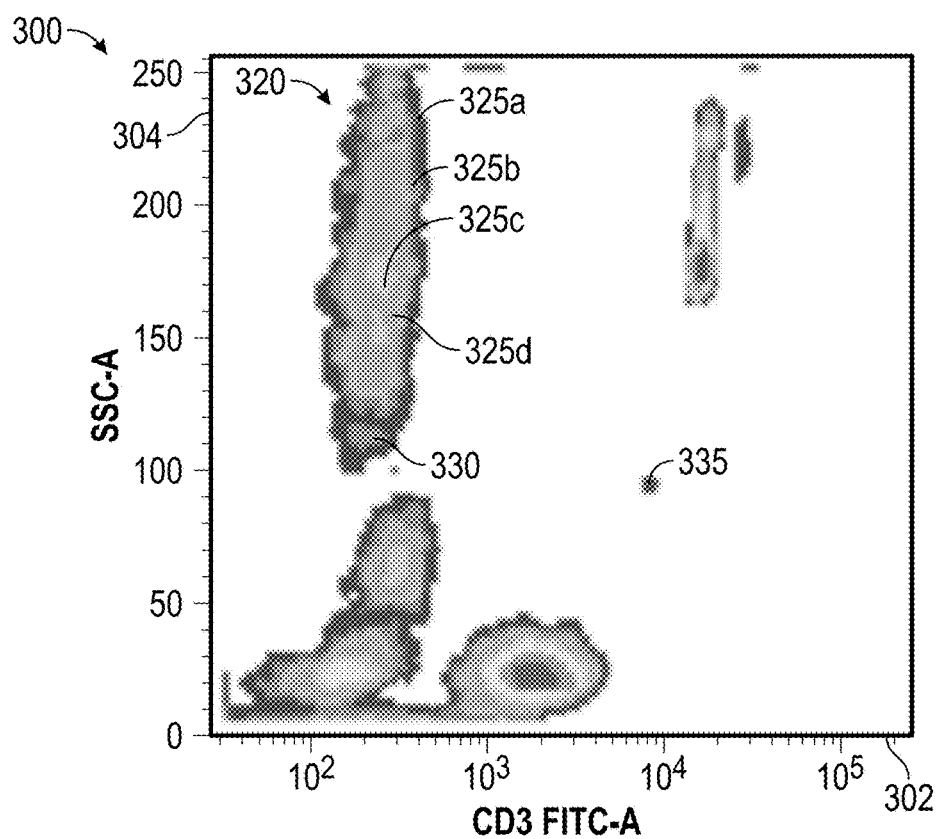
FIG. 3 shows an example of a 2D density plot diagram.

FIG. 3 shows an example of a 2D density plot diagram. The 2D density plot diagram 300 shows the density of data using two parameters plotted against each other. As with FIGS. 1 and 2, an x-axis 302 shows the parameter values while a y-axis 304 illustrates the side scatter count level. Additionally, the 2D density plot diagram 300 can include density information for areas in the diagram. For example, the 2D density plot diagram 300 includes a cluster of data 320. The cluster of data 320 may include several regions, each region associated with a common density. As shown in FIG. 3, four regions 325a, 325b, 325c, and 325d are shown. In some implementations, each region may be graphically presented using a different color.

While the 2D density plot diagram 300 provides context for the related densities, the density information is presented in a relatively raw format. As such, visual artifacts may be included in the representation. As shown in FIG. 3, a pocket 330 of a data at a given density may be formed. A cluster 335 of outliers is also shown in FIG. 3. These artifacts in the 2D density plot diagram 300 may be due to noise, calibration error, or other characteristics of the data.

Figure 4A:
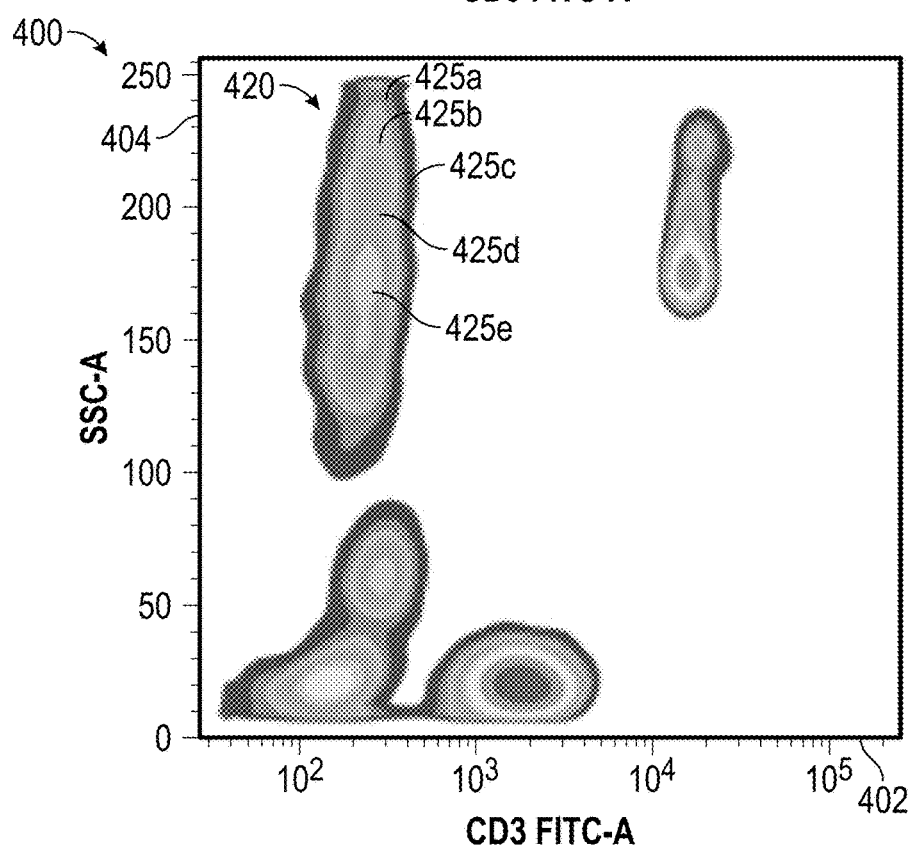
FIG. 4A shows an example of a contour plot diagram.

FIG. 4A shows an example of a contour plot diagram. The contour plot diagram 400, like the 2D density plot diagram 300, provides a visual representation useful for making sense of the data in a plot of flow cytometry data. The contour plot diagram 400 can be a better choice for display of the data because the contour plot diagram 400 uses less memory than the 2D density plot diagram 300. Furthermore, contour plot diagrams generally smooth the distracting visual artifacts discussed in reference to the 2D density plot diagram 300.

The contour plot diagram 400 shown in FIG. 4A includes an x-axis 402 showing the parameter values and a y-axis 404 illustrating the side scatter count level. Additionally, the contour plot diagram 400 can include density information for areas in the diagram. For example, the contour plot diagram 400 includes a cluster of data 420. The cluster of data 420 may include several regions, each region associated with a common density. In FIG. 4A, five regions 425a, 425b, 425c, 425d, and 425e are shown. In some implementations, each region may be graphically presented using a different color. Absent from the contour plot diagram 400 shown in FIG. 4A are the visual artifacts discussed in reference to FIG. 3.

The contour plot is a tool that allows the display of two dimensional data. It uses a two-dimensional array of values that contain the event counts for the histogram. What makes the contour useful is that a series of contours (e.g., slices) in the z-direction are made that show the levels of the data. This is a similar process as is used to create a topological map. Each level may then be assigned a color or other visual discriminator. The resulting display is a collection of polygons that may be colored according to the level of the data.

To decide what levels to use for a given set of flow data depends on the flow data itself. For example, a topographical map might have levels every 10 feet in altitude. This would be considered a linear algorithm. There are several methods that can be used to calculate the levels for displaying the contour and density levels of flow cytometric data.

One method is probability density. In the probability density approach, each level of the contour plot diagram contains roughly the same percentage of data. Another method is linear density. In a linear density implementation, the maximum level may be divided by the number of levels to determine the value. A third example is logarithmic density. In such implementations, the levels are calculated using a logarithmic algorithm. The logarithmic density method may be well suited for emphasizing lower-level data. This can allow a researcher to discriminate between fine distinctions for certain parameters and certain ranges.

Based at least in part on the data, a contour level method is selected. The selection may consider one or more of the density of the data, the number of events, the number of parameters, the analysis being performed, or the like. To create the levels used by the contour a value is set that determines how many levels are created. This may be a percentage value. In such implementations, when the probability density method is selected, a default percentage may be ten percent. The resulting contour plot diagram may include ten levels with approximately ten percent of the data being shown on each level.

Figure 4B:
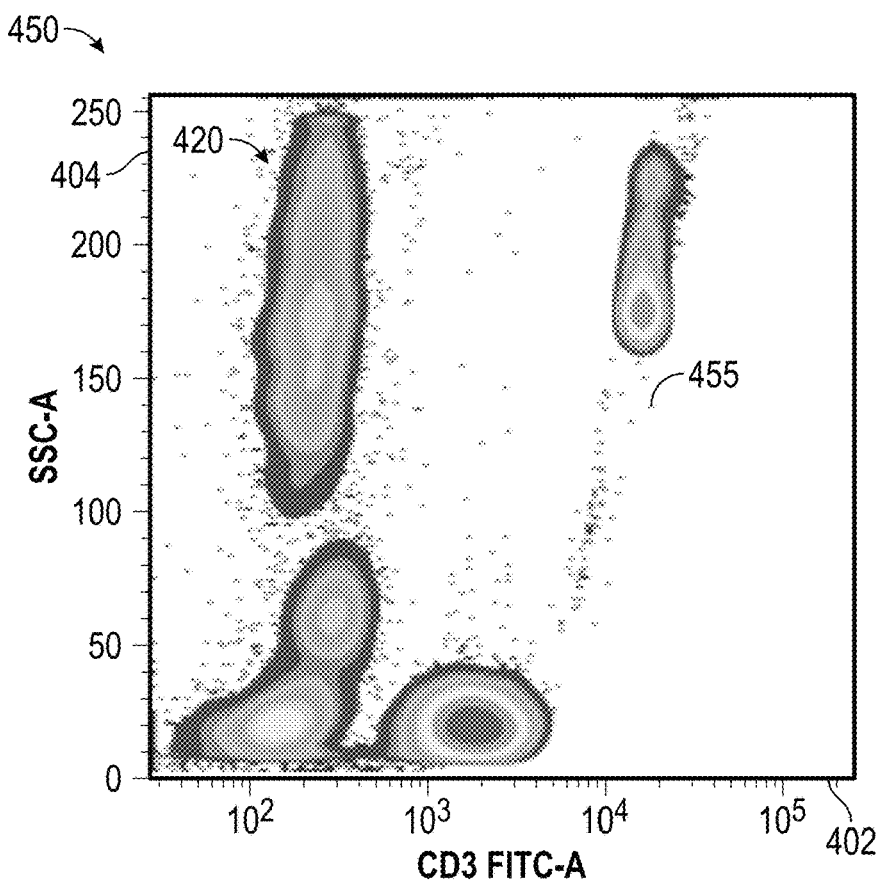
FIG. 4B shows an example of another contour plot diagram.

FIG. 4B shows an example of another contour plot diagram. The contour plot diagram 450 is substantially similar to that shown in FIG. 4A. However, the contour plot diagram 450 in FIG. 4B includes outlier data. For example, the contour plot diagram 450 includes an outlier 455. These outliers represent the events which are not included in the contours for the levels assigned to the contour plot diagram 450.

While a contour plot diagram may provide a more memory efficient representation of the flow data than other diagrams, the underlying contour data is generated based on the full set of flow data. This can result in a complex contour plot diagram which presents display and manipulation challenges. Contour algorithms typically return a collection of polygons and line segments. There is typically one polygon per tile where a tile is the unit of resolution of the contour. The number of lines and polygons can easily range into the tens of thousands or even hundreds of thousands. For a graphics system that uses immediate mode graphics, such as Win32, this may not be an issue for drawing. However, for a retained mode graphics system such as Windows Presentation Foundation, the graphics subsystem simply cannot hold tens of thousands of objects efficiently. The result will be sluggish performance along with high memory usage.

Figure 5:
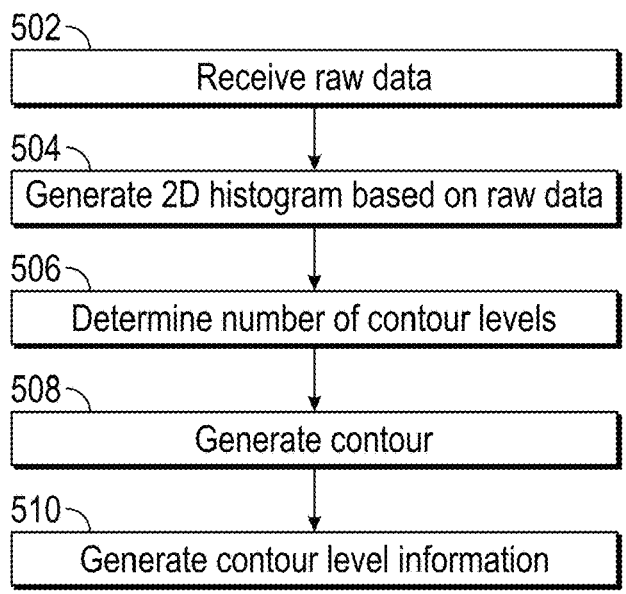
FIG. 5 shows a process flow diagram of an example of a method for processing cytometry data.

FIG. 5 shows a process flow diagram of an example of a method for processing cytometry data. The process shown in FIG. 5 can be used to generate an efficient contour along with information for each contour level. The process shown in FIG. 5 is efficient in that the contour generated consumes significantly fewer resources to store, transmit, receive, and display than other contour methods. Furthermore, the process shown in FIG. 5 is efficient in that information is generated for each contour level as part of the process. This provides a procedural efficiency to the generating process over other methods of processing cytometry data.

Generation of a contour generally includes receiving as an input a two-dimensional histogram and outputting a collection of polygons that represent the z-level of the data. To effectively display a contour, the resources needed to represent, transmit, and display the created the contour should be kept to a minimum in order to allow rendering of the polygons quickly and with limited processing, bandwidth, and/or power utilization. This may be especially important during real-time data acquisition. Furthermore, this may be important when viewing contour data on a mobile device such as a smart phone or tablet computer where battery life and bandwidth may be limited.

A typical contour algorithm can generate tens of thousands of polygons that require a lot of memory to store, high levels of bandwidth to transmit, increased processing time to receive and render and generally provides a slow user experience. To reduce the memory load, a polygon mesh-reduction (described in further detail below) can be used to remove redundant points thus reducing the polygon count. Additionally, once a single polygon is created, information for a particular contour may be generated. The information can include one or more of a number of events included within the polygon, a percentage of total events included in the polygon, a total number of events, a descriptive label for uniquely identifying the polygon, a level, a visual cue, and the like. Table 1 below provides some experimental results illustrating the efficiency gains which may be achieved using one or more of the described features.

TABLE 1

| Contour Size | Contour Metric | Without Mesh Reduction | With Mesh Reduction | Percent Reduction |
|---|---|---|---|---|
| 64 by 64 | Number of Polygons | 5372 | 24 | 99.55% |
| 64 by 64 | Draw Time (msec) | 130 | 4 | 96.92% |
| 128 by 128 | Number of Polygons | 11844 | 48 | 99.59% |
| 128 by 128 | Draw Time (msec) | 182 | 9 | 95.05% |

The method shown in FIG. 5 begins at node 502 by receiving the raw cytometry data. As discussed, this data may be flow cytometry data. The data may be received from a network location, a memory location (e.g., disk, USB drive, CD-ROM, DVD, cloud storage, etc.), or through one or more wired or wireless communication channels from another electronic device. The data may be "raw" in the sense that the information is simply a list of events for one or more parameters. The data may be formatted such as to facilitate computer processing, by the cytometer. However, the data may not include summary, context, or other refinements which can allow a researcher to analyze and make decisions based on the information.

At node 504, a 2D histogram of the received data is generated. The 2D histogram provides an organization to the raw data by grouping events into one or more bins. This may, in some contexts, be referred to as quantization.

At node 506, a number of contour levels is determined. The number of contour levels may be determined using, for example, linear, percentage, or logarithmic methods described above. The determination may be based on characteristics of the data such as number of events, density of the data, parameters of interest, pre-determined user preferences (e.g., preference for a method), assay being performed, and the like. Each method may further include parameters to generate the levels. For example, the percentage method may also need a percent value. These additional parameters may be determined based on the data, pre-defined such as a user preference or default values, or by receiving additional inputs of the parameters.

At node 508, a contour is generated based on the received 2D histogram of data and the determined contour levels. The method of generating the contour is described in further detail below in reference to FIG. 6.

At node 510, information is generated for each contour level. The information may include one or more of a number of events included within the polygon, a percentage of total events included in the polygon, a total number of events, a descriptive label for uniquely identifying the polygon, a level, a visual cue, and the like. In some implementations, the information may be generated in parallel as polygons for the contour are generated by node 508.

In some implementations, the generated contour and generated contour information may be stored for further processing such as display. In some implementations, the generated contour and/or generated contour information may be transmitted to another electronic device. For example, a tablet computer may transmit a message including an identifier of a set of raw data to display. Using this identifier, the system may perform the process shown in FIG. 5 and transmit the generated contour and generated contour level information to the tablet computer.

Figure 6:
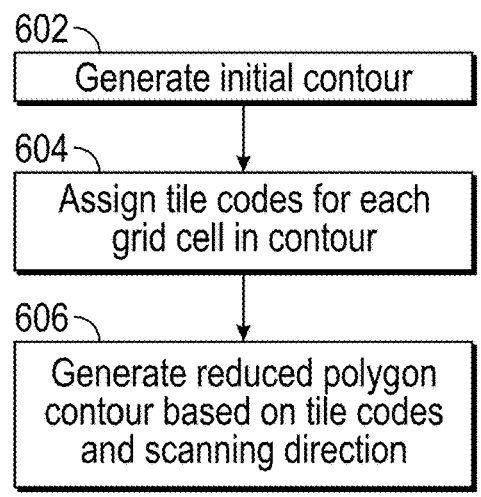
FIG. 6 illustrates a process flow diagram for an example of a method for generating a contour.

FIG. 6 illustrates a process flow diagram for generating a contour. More specifically, the process shown in FIG. 6 illustrates how an efficient contour may be generated.

At node 602, an initial contour is generated. In some implementations, the initial contour may be provided as an input. In some implementations, the contour may be generated using, for example, any one of the described contour methods above. One non-limiting advantage of the process shown in the process is applicable to generate efficient contours from any contour.

Figure 7:
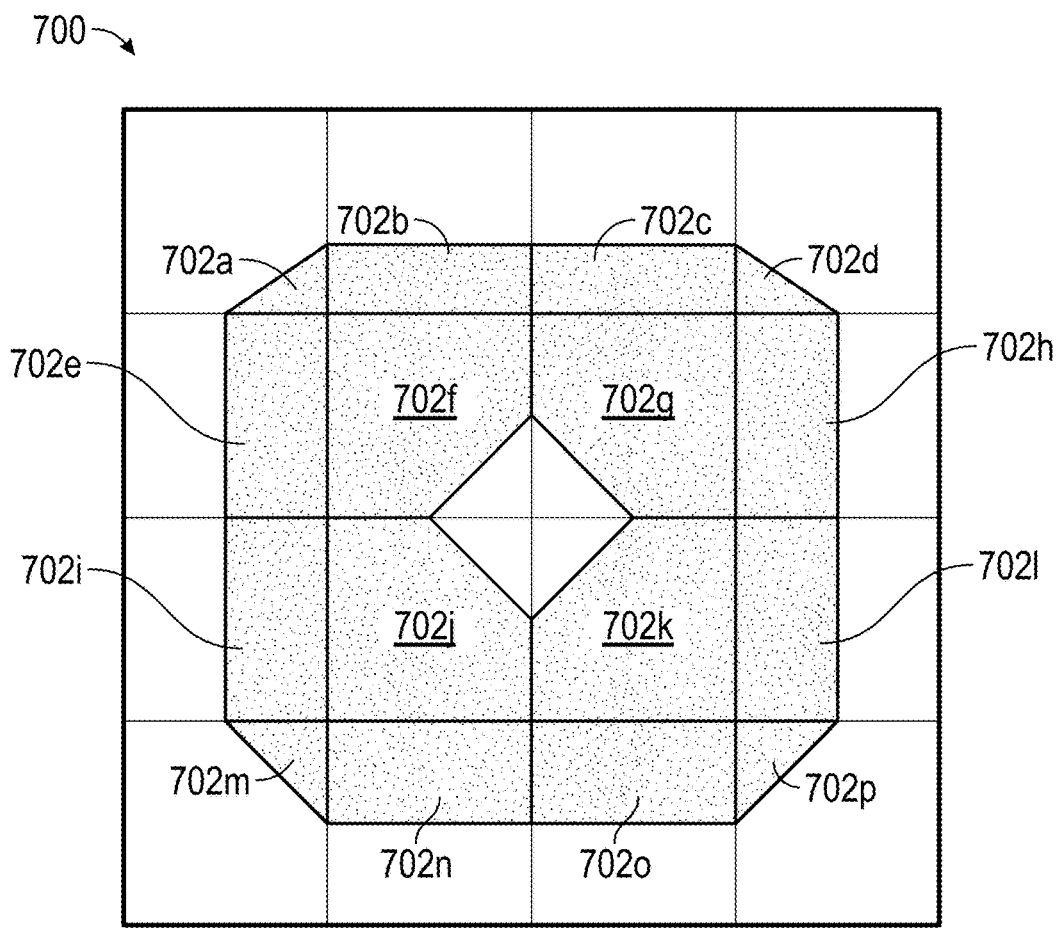
FIG. 7 shows an example initial contour diagram.

FIG. 7 shows an example initial contour. The initial contour 700 is divided into a four by four grid. Each box in the four by four grid may be referred to as a tile or grid cell. Each tile may include a polygon representing event data. The initial contour 700 shown includes sixteen polygons 702a-702p, one per each cell. Each polygon may be represented by three or more points. To represent all the polygons in the contour shown in FIG. 7, sixty-four points are used. While the initial contour 700 in FIG. 7 is a relatively small contour, as the amount of data is increased, the number of tiles and polygons contained therein can substantially increase. These increases present an opportunity to improve the contour representation.

Returning to FIG. 6, at node 604, each grid cell of the initial contour 700 is represented by a tile code depending on the corner values for the grid cell and the contour level associated with each corner value. The tile code indicates how the polygon(s) for a particular cell are calculated. The tile code is generated based on the four corner points for a cell. Each corner point may be greater than or equal to the current contour level, or less than the current contour level. If the corner value is greater than or equal to the current contour level, the values near that corner should be included in the current contour level. If the corner value is less than the current contour level, the values near that corner should not be included in the current contour level.

Tile codes may be represented using four binary numbers, each number representing one corner of a tile.

Figure 8:
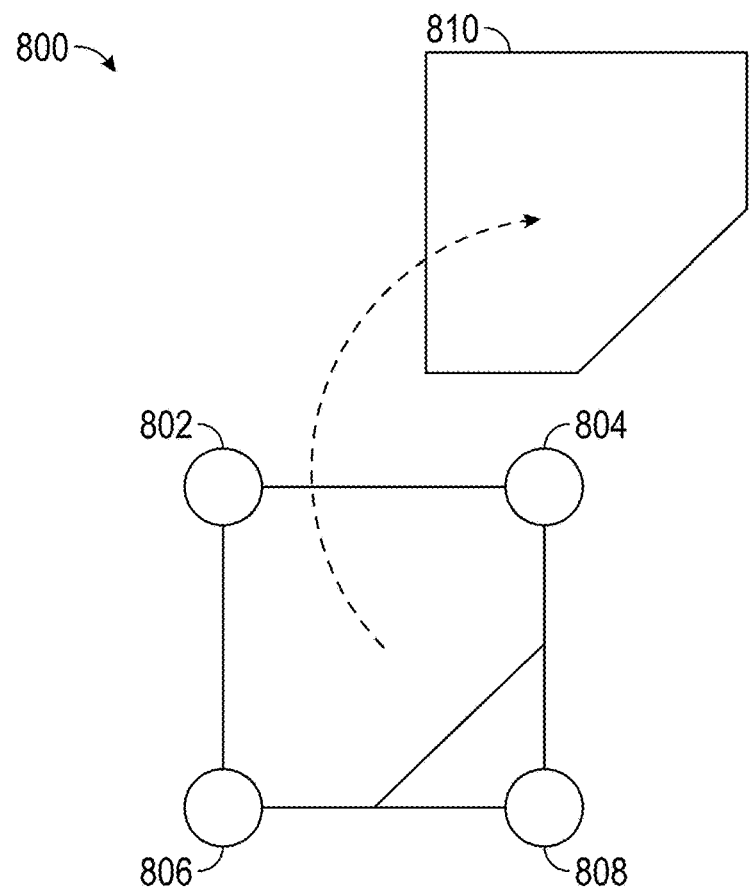
FIG. 8 illustrates an example of a tile code mapping.

FIG. 8 illustrates an example of a tile code mapping. The tile code mapping 800 shown in FIG. 8 may be for the tile code "1101." The tile code mapping 800 shown includes four corner points 802, 804, 806, and 808. As shown, corners 802, 804, and 806 have values that are greater than the contour level. Accordingly, these corners may be identified using a first binary value such as "1". Corner 808 is less than the current contour value. Accordingly, this corner may be represented using a different binary value such as "0". As a result, in this example, the tile code assigned to this tile is "1101". This tile code identifies a polygon 810 that will have five points.

Figure 9A:
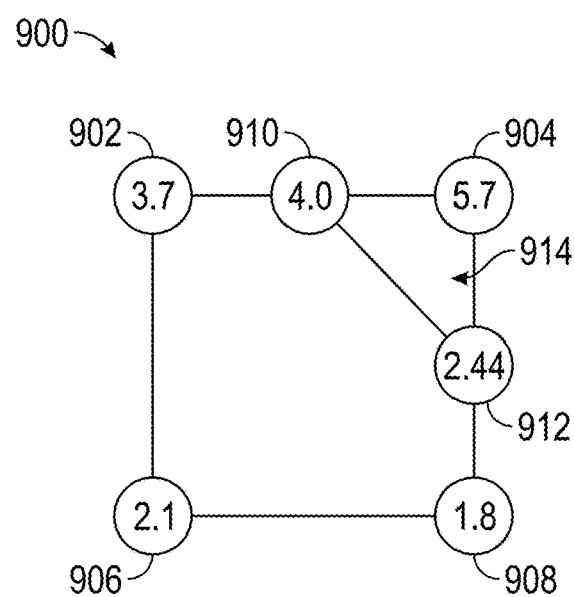
FIG. 9A illustrates a further example of a tile code mapping.

FIG. 9A illustrates a further example of a tile code mapping. The mapping shown in FIG. 9A includes corner values for each corner 902, 904, 906, and 908 (3.7, 5.7, 2.1, and 1.8 respectively) for a tile 900. For the example shown in FIG. 9A, the desired contour level is 4.3. For the first corner 902, the corner value (3.7) is less than the desired contour level (4.3). The tile code can include a "0" in the first position indicating this. For the second corner 904, the corner value (5.7) is greater than the desired contour. The tile code can include a "1" in the second position indicating this. The third corner 906 value (2.1) is less than the desired contour level and thus may be represented by a "0" in the third position of the tile code. The final corner 908 has a value (1.8) that is also less than the desired contour level. Thus, the final corner 908 may be represented using a "0" in the last position of the tile code. The resulting tile code for the tile shown in FIG. 9A is "0100". While binary is used in this example, the tile code may be represented using other formats such as decimal, hex-decimal, delimited, or other machine readable formats.

Having identified the corner point(s) included in the contour level for the tile 900, two additional points 910 and 912 may be generated based on linear interpolation between the corner points. A polygon 914 forming a triangle is thus represented for this tile 900. The polygon 914 identifies a portion of the contour level included in the tile 900.

Figure 9B:
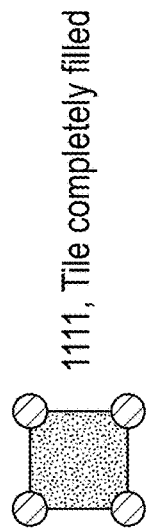
FIG. 9B shows another example of a contour mapping convention which may be implemented in the systems and devices described herein.
Figure 9B:
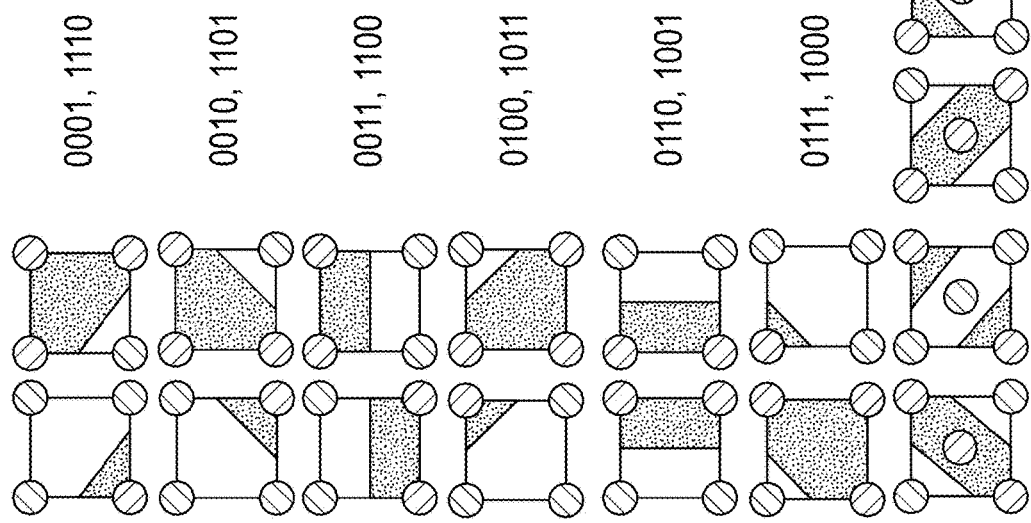

FIG. 9B shows another example of a contour mapping convention which may be implemented in the systems and devices described herein. The convention shown in FIG. 9B includes a contour code for each tile. The code format includes four elements, one element per corner of a tile. FIG. 9B assigns the upper-left corner as the first element (element 0) and proceeds in a clock-wise fashion to incrementally number the points. Each element may be represented by one of two values, a "0" or a "1". As used in the convention in FIG. 9B, if the element for a corner point includes a "0", the corner point is less than the current contour level. If the element for a corner point includes a "1", the corner point is greater than or equal to the current contour level. At one end of the spectrum, a tile associated with the code "0000" is entirely below the current contour level. At the other end of this spectrum, a tile associated with the code "1111" is entirely within the current contour level. FIG. 9B includes intermediate permutations in accordance with the convention described.

After producing the points for the contour level, the resulting polygons could be provided for display. However, as discussed earlier, the contour results in a very large data structure that may not permit, for example, fast rendering to a display or fast downloads of the contour over an Internet connection.

Returning to FIG. 6, at node 606, the polygons included in the contour are reduced. Polygon reduction is accomplished by matching adjacent polygons and their points and consolidating the common points. This yields a larger polygon including fewer points.

Figure 10A:
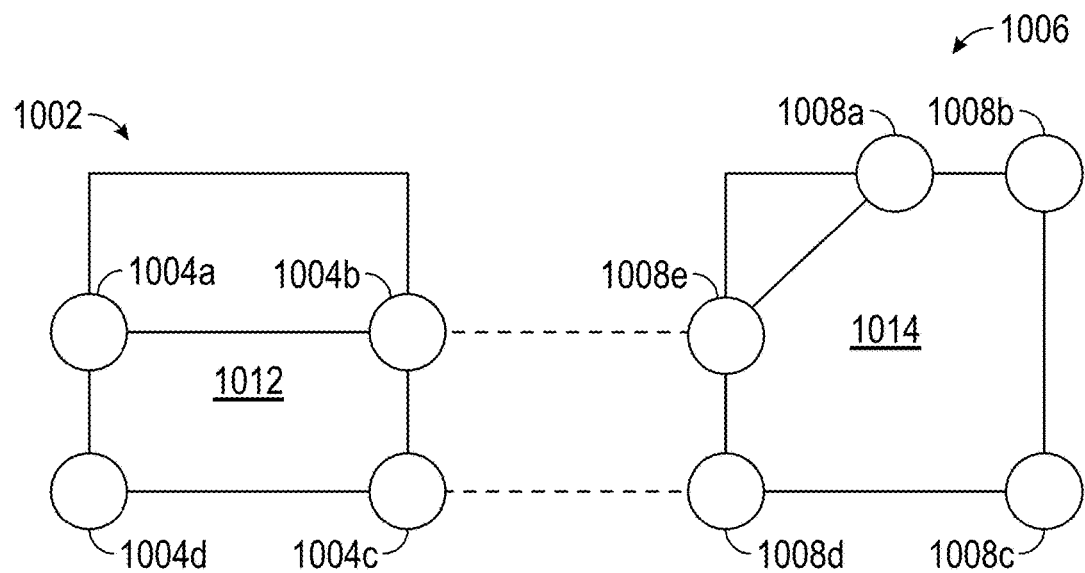
FIG. 10A shows two adjacent tiles in the contour.
Figure 10B:
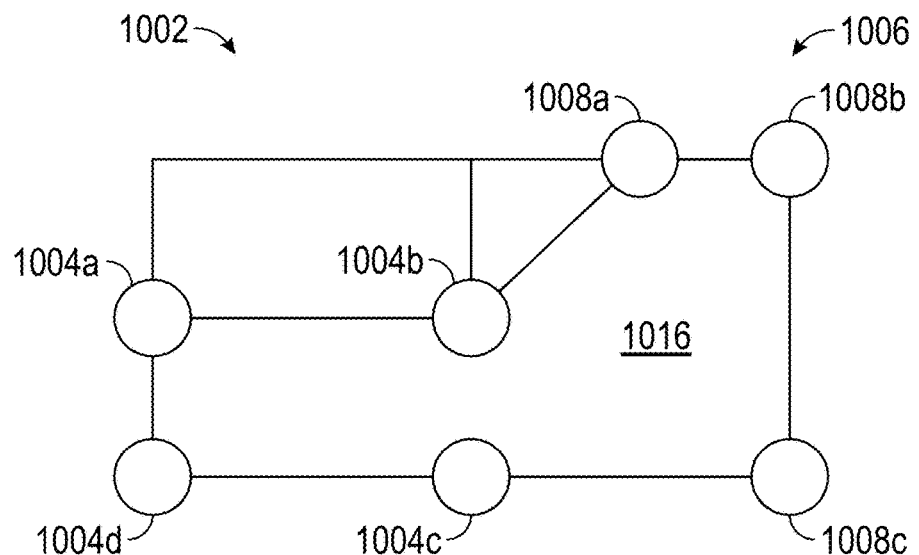
FIG. 10B illustrates two adjacent tiles including a reduced polygon.

FIGS. 10A and 10B illustrate adjacent tiles before and after reduction, respectively. FIG. 10A shows two adjacent tiles in the contour. A first tile 1002 includes a polygon 1012 including four points 1004a-1004d. A second tile 1006 includes another polygon 1014 five points 1008a-1008e. Points 1004b and 1004c from the first tile 1002 have substantially the same value as points 1008d and 1008e from the second tile 1006. These overlapping points represent redundant data.

FIG. 10B illustrates two adjacent tiles including a reduced polygon. The overlapping points are considered once and a single polygon 1016 is represented in the contour. As shown, the values for the points 1004b and 1004c from the first polygon 1002 are retained. In some implementations, the values from the current tile are retained. In some implementations, the values from the adjacent tile are used. This reduces the number of points used to represent the polygon from nine to seven. These savings are especially significant when representing larger polygons over many tiles.

The reduction performed by node 606 of FIG. 6 may be based on whether the tile has 'compatible' polygons adjacent to the left or on top. If it is determined that there are indeed compatible polygons for adjacent tiles, then the polygons can be are combined. This process may start in the upper-left corner and proceeds to the right and down. It will be understood that other scanning patterns may be used with similar effect.

It may seem that there are endless combinations of how the polygons might be combined but the set of combinations is actually much smaller. The actual cases can be classified by determining if the tile can be combined with: the left tile only; the top tile only; the left and top tiles; or no tiles in which case, the start of a new polygon is identified.

Figure 17:
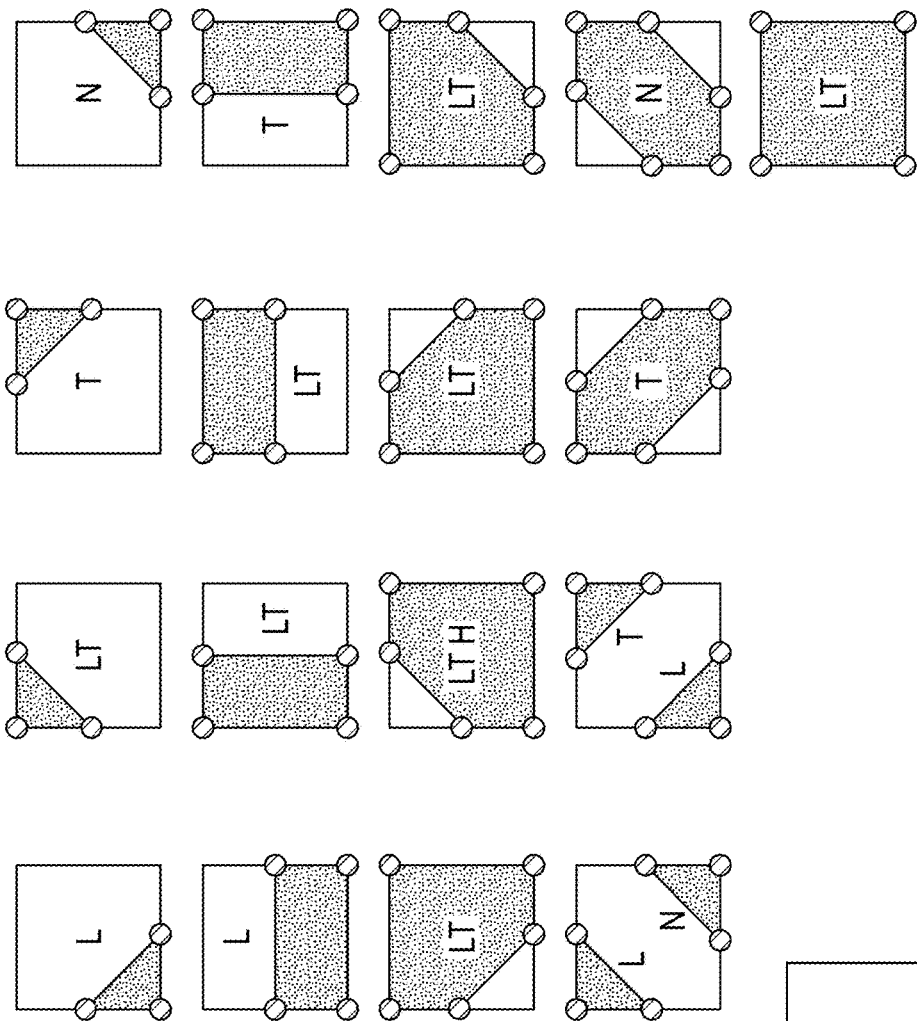
FIG. 17 shows examples of compatible locations for combining tiles.

Based on a tile scanning pattern and the tile code for a given tile, the direction(s) to look for compatible polygons may be determined. For example, in one implementation, a left-to-right, top-to-bottom scanning pattern may be used. For a tile having the code "1101" as shown in FIG. 8, the adjacent polygons may exist above or to the left. For a tile having the code "0100" as shown in FIG. 9A, the adjacent polygons may exist above. FIG. 17, discussed in further detail below, provides further examples of conventions for determining compatible locations for various tiles.

Figure 11:
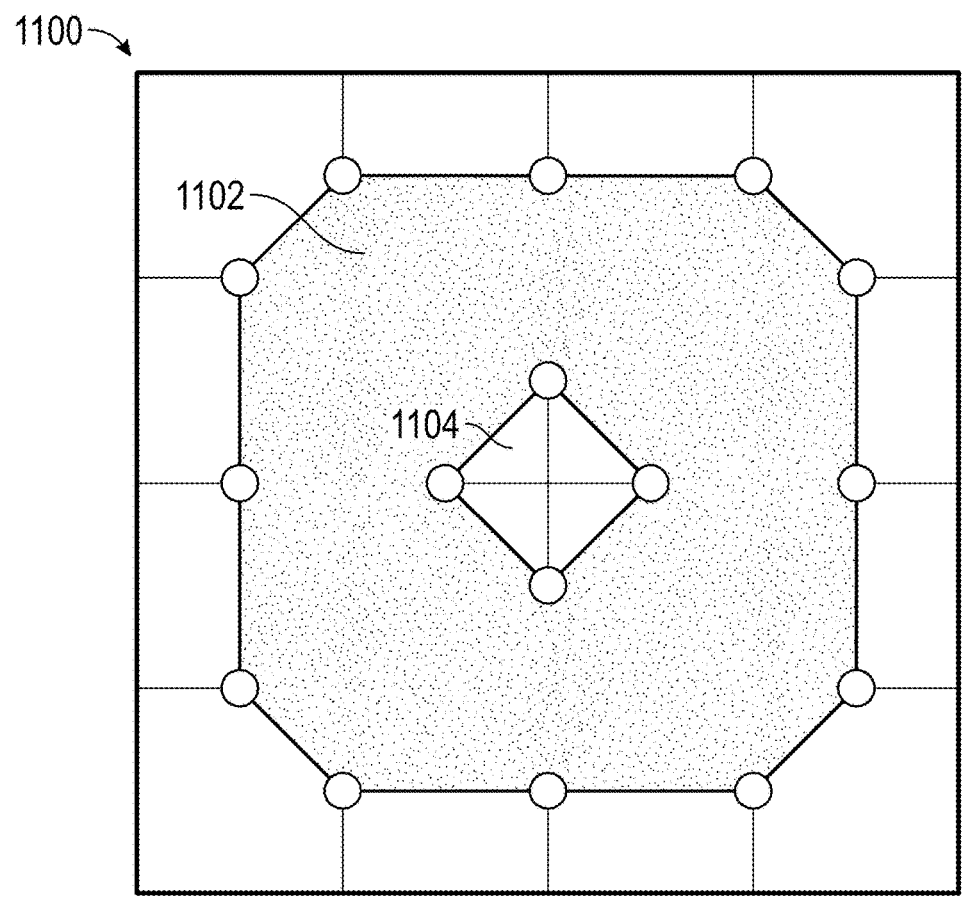
FIG. 11 shows an example reduced contour diagram.

FIG. 11 shows an example reduced contour diagram. The reduced contour 1100 is a reduced version of the initial contour 700 shown in FIG. 7. The reduced contour 1100 includes two polygons 1102 and 1104 represented using sixteen points.

Figure 12:
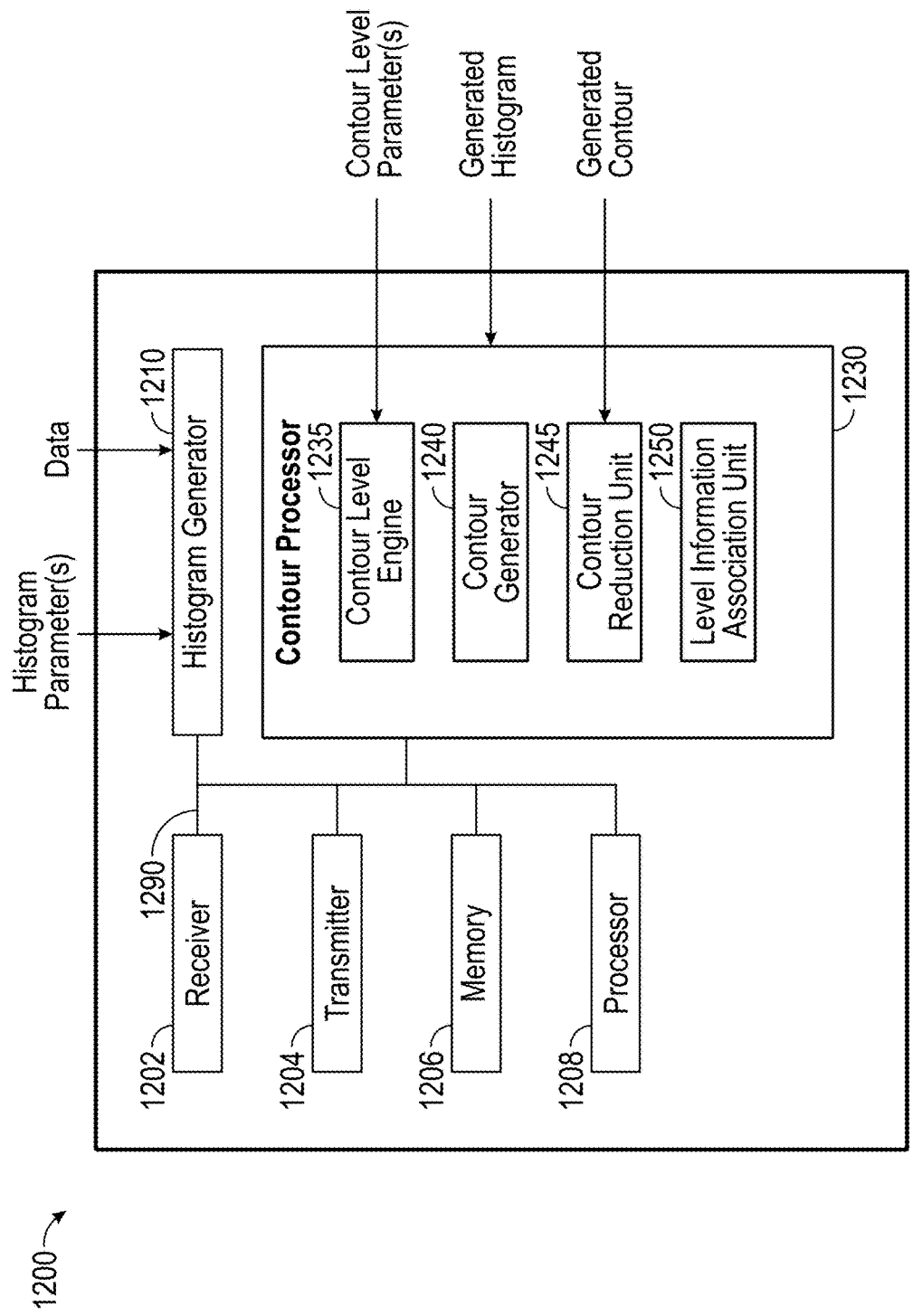
FIG. 12 shows a functional block diagram for one example of an electronic device for efficient processing of cytometry data.

FIG. 12 shows a functional block diagram for one example of an electronic device for efficient processing of cytometry data. The electronic device 1200 may be configured to implement one or more aspects of the processes shown in FIGS. 5 and/or 6 and as described above.

The electronic device 1200 includes a receiver 1202. The receiver 1202 is configured to receive information for further processing by the electronic device 1200. For example, the receiver 1202 may receive raw flow cytometry data. The receiver 1202 may also receive parameters to control the operational characteristics of the electronic device 1200. The receiver 1202 may also receive processed flow data such as histograms or contours. The receiver 1202 may be configured to receive messages from another electronic device such as a table computer or smartphone.

The receiver 1202 may be implemented as a wired or wireless receiver. In a wireless implementation, the receiver 1202 may include an antenna and a signal processor. In a wired implementation, the receiver 1202 may include one or more of a network interface, physical connections (e.g., Ethernet, USB, HDMI, telephone, etc.), and an application programming interface to the various features described.

The electronic device 1200 may include a transmitter 1204. The transmitter 1204 may be configured to transmit information generated or otherwise acquired by the electronic device 1200. One example of information that may be transmitted by the transmitter 1204 is a reduced contour plot.

The transmitter 1204 may be configured to format the data for transmission. The formatting may include one or more of packetization, encapsulation (e.g., in a machine readable format such as XML; JSON; delimited text; binary format such as bitmap or other image file format; and the like), encryption, and compression.

The transmitter 1204 may be configured for wired or wireless transmission. In a wireless implementation, the transmitter 1204 may include a signal generator, amplifier, and antenna. In a wired implementation, the transmitter 1204 may include one or more of a network interface and physical connections (e.g., Ethernet, USB, HDMI, telephone, etc.).

The electronic device 1200 may include a memory 1206. The memory 1206, which may include read-only memory (ROM) and/or random access memory (RAM), may store information received by the electronic device 1200. The memory 1206 may also store information generated by the electronic device 1200. A portion of the memory 1206 may also include non-volatile random access memory (NVRAM).

The electronic device 1200 may also include a processor 1208. The processor 1208 may control and/or coordinate operation of the electronic device 1200. In some implementations, the processor 1208 may be referred to as a central processing unit (CPU). The processor may be configured to transmit messages to one or more of the components of the electronic device 1200. The processor may also be configured to receive messages from one or more of the components of the electronic device 1200.

The processor 1208 may be implemented with any combination of general or special purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

The memory 1206 may provide instructions and data to the processor 1208. The processor 1208 may be configured to perform logical and arithmetic operations based on program instructions stored within the memory 1206. The instructions in the memory 1206 may be executable to implement the methods described herein.

The electronic device 1200 shown in FIG. 12 includes a histogram generator 1210. The histogram generator 1210 is shown as receiving two inputs, histogram parameter(s) and data. In some implementations, these inputs may be stored in the memory 1206. In some implementations, one or both of these inputs are received externally such as via the receiver 1202 based on a received message.

The histogram generator 1210 may be configured to generate a 2D histogram for the provided data. The histogram generated may be based on the histogram parameter(s) provided to the histogram generator 1210. For example, the number of bins for the histogram may be included in the histogram parameter(s). In some implementations, the histogram generator 1210 may be configured to dynamically determine histogram parameter(s) based on the input data. For example, the number of events included in a set of flow cytometry data may be used to identify the number of bins.

The histogram generator 1210 may be configured to store the generated histogram in the memory 1206.

The electronic device 1200 includes a contour processor 1230. The contour processor is configured to process contours as described herein. The contour processor is configured to receive a generated histogram as an input. The generated histogram may be received via the receiver 1202 or from the histogram generator 1210. The generated histogram may be obtained either directly from its source or via the memory 1206.

The contour processor 1230 shown in FIG. 12 includes a contour level engine 1235. The contour level engine 1235 is configured to identify an appropriate contour determination method and number of levels for a contour. The contour level engine 1235 may receive one or more contour level parameter(s). For example, a percentage value for use in a percent density contour may be provided. In some implementations, the contour level engine 1235 may be configured to dynamically determine contour level parameter(s) based on the input data. For example, the number of events included in a set of flow cytometry data may be used to identify the percentage. In some implementations, the contour level parameter(s) may be stored in the memory 1206. In some implementations, one or more contour level parameter(s) may be received externally such as via the receiver 1202 based on a received message.

The contour processor 1230 shown includes a contour generator 1240. The contour generator 1240 may utilize one or more of the generated histogram, contour level(s) identified by the contour level engine 1235, and the contour level parameter(s) to generate contour as described above. The contour generator 1240 may be configured to store the generated contour in the memory 1206. In some implementations, the contour generator 1240 may be configured to cause the transmitter 1204 to transmit the generated contour. As discussed, the generated contour may be a large structure which may present several challenges especially in limited resource environments.

Accordingly, the electronic device 1200 may include a contour reduction unit 1245 in the contour processor 1230. The contour reduction unit 1245 may be configured to generate an efficient representation of a contour such as a contour generated by the contour generator 1240. In some implementations, the contour reduction unit 1245 may receive a contour previously generated. For example, a contour may have been previously generated and stored in memory. The contour reduction unit 1245 may obtain this contour and generate a reduced representation as described above.

The contour reduction unit 1245 may be configured to store the generated contour in the memory 1206. In some implementations, the contour reduction unit 1245 may be configured to cause the transmitter 1204 to transmit the generated contour.

The contour processor 1230 shown also includes a level information association unit 1250. The level information association unit 1250 may be configured to generate information for one or more levels included in the generated contour. The level information may include a number of events included within the polygon, a percentage of total events included in the polygon, a total number of events, a descriptive label for uniquely identifying the polygon, a level, a visual cue (e.g., color, icon, fill pattern), and the like.

The level information association unit 1250 may be configured to store the generated level information in the memory 1206. In some implementations, the level information association unit 1250 may be configured to cause the transmitter 1204 to transmit the generated level information either with the associated contour or separate from the associated contour.

The above described elements of the electronic device 1200 may be coupled by a bus 1290. The bus 1290 may be a data bus, communication bus, or other bus mechanism to enable the various components of the electronic device 1200 to exchange information. In some implementations, the bus 1290 may facilitate the transfer of power among the elements shown. It will further be appreciated that while different elements have been shown, multiple elements shown may be combined into a single element.

Being able to efficiently generate and represent contours can provide several further benefits. For example, on-demand statistics may be provided for each contour level. In one implementation, as the user moves a pointer over the contour, the statistics for that contour may be provided in a "popup" display window. The process of obtaining the statistics can be very dynamic and practically instantaneous. As soon as an input signal identifying a contour level is received, the statistics for the identified contour may be transmitted. The contour level that is associated with the received signal can be highlighted or otherwise cause a visual cue to be generated which indicates the selected contour level.

Using the described features allows a researcher to quickly understand where the data is. In an implementation where the probability density is 10%, the percent total statistic for each of the three main regions shown sums to 90%. That is, the three main regions represent levels for 90% of the flow data in this set. The remaining 10% are outliers. These features allow users to immediately understand where the data is and how much is there—an important aspect of reading a flow cytometry result report.

Some researchers may prefer to see the events as dots instead of the contours. Because the contour information is efficiently represented, the contour information can be used in conjunction with a dot-plot to augment the dot display. For example the described systems and methods allow the generation of a hybrid contour-dot-plot that displays the individual events as dots but has the coloring of the contour. The coloring may be based on the information included in the reduced contour generated as described above. In addition, the on-demand statistics associated with the contour levels are also available. In some implementations including the hybrid plot, the researcher may view a dot-plot diagram with density coloring of the dots. Also the researcher can see the statistics for a region of dots using the contour outlines that are invisible.

A further implementation of the described systems methods includes creating gates. Typically, the researcher will create a gate around data of interest. Density plots are useful for gating data since area of data that are dense usually indicate important data. The researcher may use one of several tools to draw geometric gates such as a rectangle, ellipse, or polygon. This process of manually 'drawing' the gate can be tedious. Furthermore, the tools may not permit drawing a precise gate as the data of interest may not be entirely geometric or easily represented using the available tools. Using the features described, a gate can be created by identifying a contour level. Using a similar technique as the on-demand statistics, the contour diagram includes information which allows a gate to quickly be created from an identified region.

The gate is generally created automatically using points that follow the contour. As the contour information is represented in reduced form, the efficiency of identifying and generating the gate is improved over standard contour gating.

Figure 13:
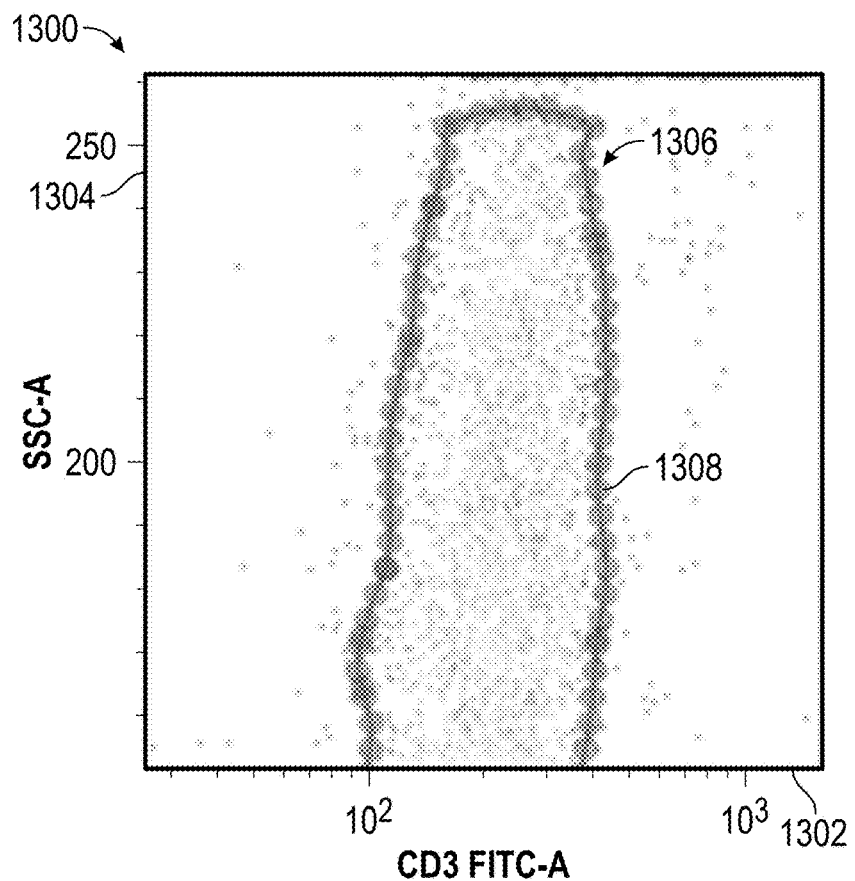
FIG. 13 shows an example of a gate for a contour plot diagram.

FIG. 13 shows an example of a gate for a contour plot diagram. The contour plot diagram 1300 shown in FIG. 13 includes an x-axis 1302 showing the parameter values and a y-axis 1304 illustrating the side scatter count level. Note, that compared to the contour plot shown, for example, in FIG. 4A, the contour plot of FIG. 13 is zoomed in such that the x and y axes present data at a smaller scale.

The contour plot diagram 1300 includes a gate 1306. The gate 1306 is comprised of a series of points. One point 1308 is identified in FIG. 13, but a gate may include hundreds or thousands of points. Ensuring the appropriate gate is selected can be tedious. Accordingly, a user may select a contour and from the contour generate a gate along the boundary of the contour.

Figure 14:
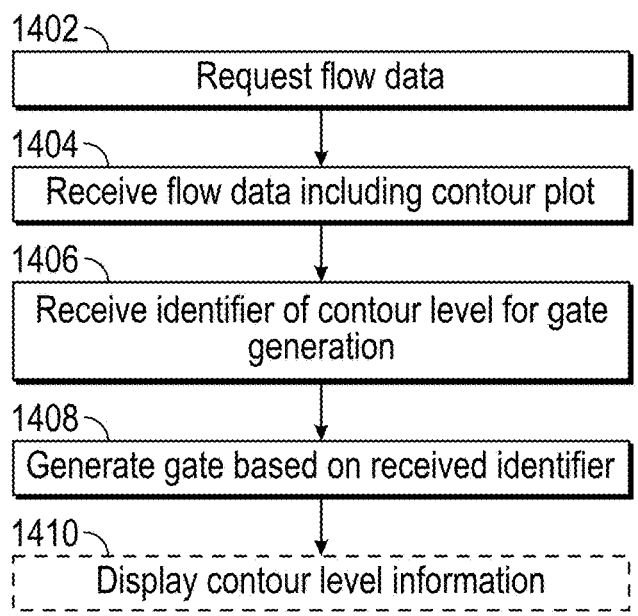
FIG. 14 shows a process flow diagram for a method of generating a gate.

FIG. 14 shows a process flow diagram for a method of generating a gate. The process shown in FIG. 14 may be implemented using an electronic communication device such as a tablet computer, laptop computer, smartphone or the like.

At node 1402, a request for flow data is transmitted. The request may include an identifier for a set of flow data to be displayed. At node 1404, the requested flow data is received. The received flow data may include a contour plot as described above. The contour plot may include one or more contour levels. The contour levels may be associated with level information such as a descriptive level label, statistics, or other information. The received flow data may be provided in a machine readable format such as XML, JSON, delimited text, a binary format such as bitmap or other image file format, and the like. In some implementations, each level may be separately identified such that the presentation of a given layer can be selectively controlled (e.g., displayed based on a received message including an identifier for a layer to show).

In some implementations, received flow data may include information for generating a dot-plot and contour information. In such implementations, the dot-plot may be displayed based on the contour information. For example, the color selected for rendering points on the dot-plot may be based on the density information included in the contour information. Accordingly, a dot-plot diagram may be generated which includes density information such as one or more contour levels. Further examples of generating a presentation of flow cytometry data are discussed below with reference to FIG. 15.

At node 1406, a message including the identifier for a contour level to use for generating the gate is received. For example, a user may tap to select a contour level and cause transmission of identifying information for the contour level to be transmitted. At node 1408, based on the received identifier for the contour level, a gate is generated for the set of data. Optionally, at node 1410, information associated with the gate associated with contour level may be displayed.

In some implementations, the process shown in FIG. 14 may include transmitting messages to a central server to obtain the information. In some implementations, the process shown in FIG. 14 may include receiving one set of flow data including one or more of the contour plot, contour levels, and contour information. The display may then include identifying which portion of the flow data to provide for presentation. Because the contour data described herein is efficiently represented, maintaining this information in memory, such as on a tablet computer, provides a suitable user experience.

Figure 15:
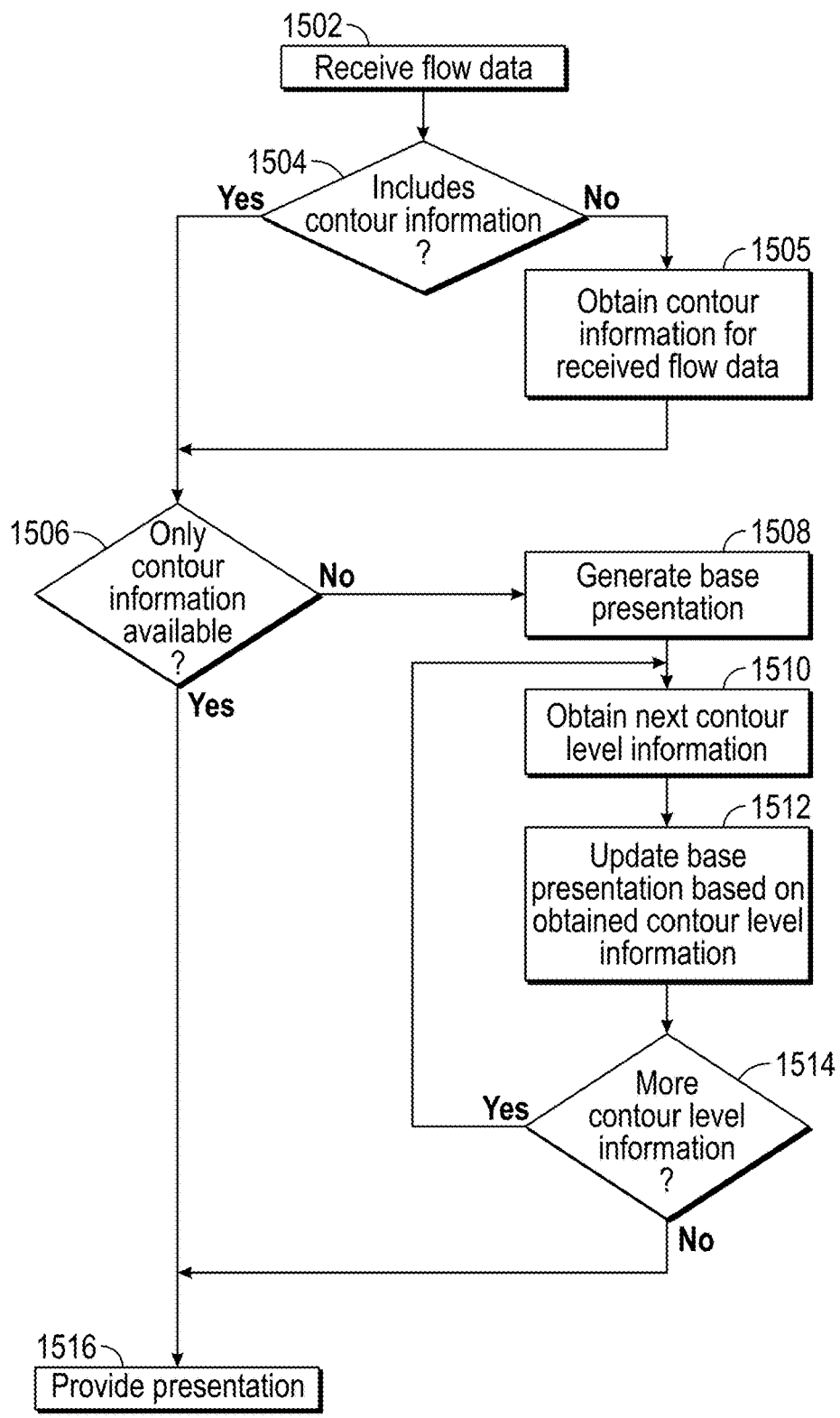
FIG. 15 shows a process flow diagram for a method of generating a presentation of flow cytometry data.

FIG. 15 illustrates a process flow diagram of a method of generating a presentation of flow cytometry data. At node 1502, flow cytometry data is received. The flow cytometry data may be received in a raw format, such as from a flow cytometer or from a memory. In some implementations receiving the flow cytometry data may include receiving an identifier for a set of flow data and obtaining the flow cytometry data based on the received identifier. The received flow data may include one or more plots such as those described above.

At decision node 1504, a determination is made as to whether the received flow cytometry data includes contour information. If the flow data does not include contour information, at node 1505 contour information is obtained for the received flow data. Obtaining the contour information may include generating a mesh reduced contour as described above. In some implementations, a request may be transmitted to obtain the contour information.

If, at decision node 1504, it is determined that the received flow data includes contour information or upon receipt of the contour information at node 1505, the process flow continues to node 1506. At decision node 1506, a determination is made as to whether the only information available is contour information. For example, only a contour plot may be available for the flow cytometry data. If this is the case, the flow continues to node 1516 where a presentation is provided which includes the contour plot. As discussed, the contour plot may include one or more contour levels. Each level may be associated with information as described above.

Returning to decision node 1506, if the contour information is available along with other flow data, such as a dot-plot, the flow continues to node 1508. At node 1508, a base presentation is generated. The base presentation may include, for example, a dot-plot diagram of the flow data. At node 1510, information for a contour level is obtained. The information about a contour level may include visual cue such as a color and/or icon for the level. The obtaining may be based on a point included in the base presentation. At node 1512, the base presentation may be updated based on the obtained contour level information. The update may include assigning a presentation color to one or more points included in the base presentation which are located within a contour level. The update may include adding an additional display layer to the presentation including the contour level information. In some implementations this layer may be transparent until selected. At decision node 1514, a determination is made as to whether further contour level information is available. If not, the flow continues to node 1516 where the presentation as updated is provided. If further contour level information is available, the process returns to node 1510 to process information for another contour level.

As shown in FIG. 15, the contour levels are iterated to update the base display. In some implementations, the contour level information may be obtained and applied to each point as the base presentation is generated. In either case, the provided presentation includes density information along with any additional flow data.

Figure 16:
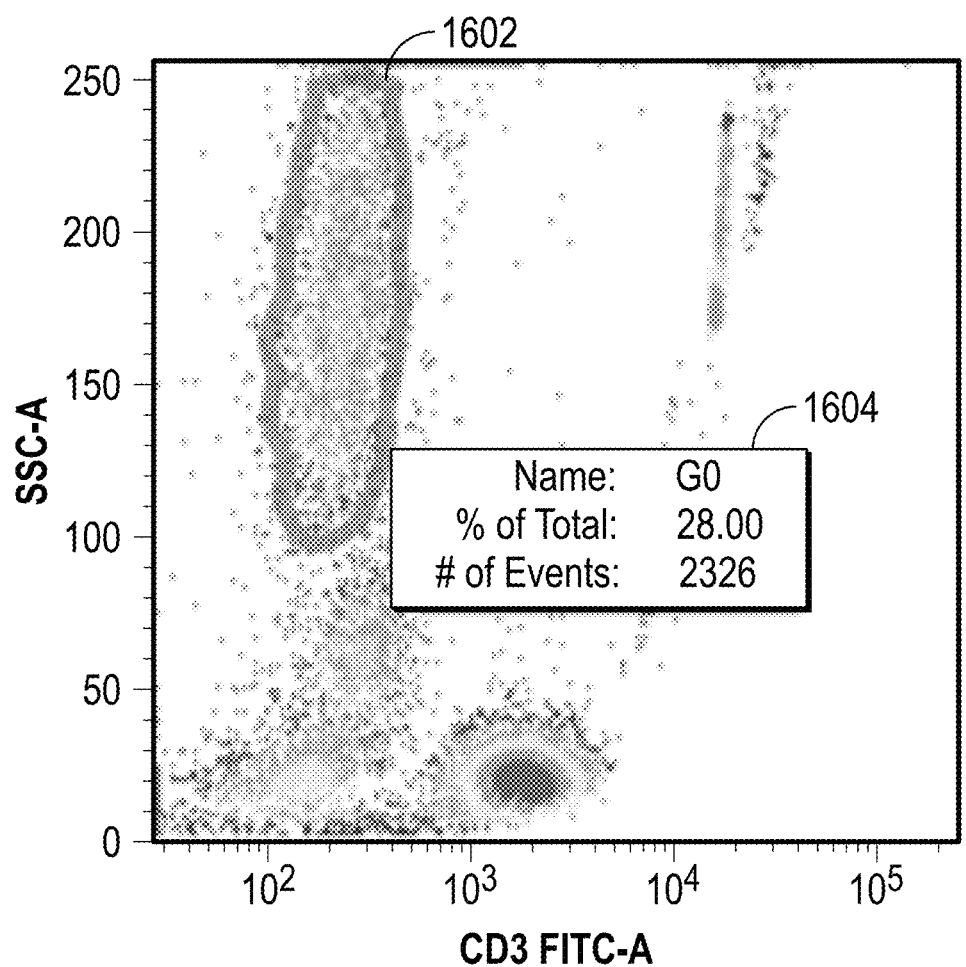
FIG. 16 illustrates an interface diagram for an example display including a gate and contour information.

FIG. 16 illustrates an interface diagram for an example display including a gate and contour information. The gate 1602 may be highlighted using a color which distinguishes the selected region from other areas of the contour plot. The contour information 1604 includes a display name, a percent of total events included in the gated region, and a number of events in the gated region. It will be understood that fewer, different, or additional information may be presented in the contour information 1604 element.

FIG. 16 also shows how a dot-plot may include the density information provided via contour information. Each of the dots included in the plot may be presented, for example, in a different color. The various shades may indicate the relative density of events at a particular region. The hybrid dot-plot/contour presentation shown in FIG. 16 may be generated using the method described in FIG. 15.

Automatic generation of the gate allows the gate to be accurately represented based on the generated contour level(s). This is much more accurate than a manually drawn gate of the same region. In addition the gate is much quicker to create accurately rather than manually creating a polygon. In some implementations, if the gate is unselected the tooltip for the gate may display the statistics for the region.

Another feature which may be implemented using the described techniques is real time contour generation. As the systems and methods described provide a smaller data set, a local contour may be generated based on a received input signal identifying a point of interest. For example, using a pre-defined tolerance range, a local contour can be generated that will be drawn around the identified point. The identification may be transmitted in response to a mouse click, tap via a touchscreen, or other gesture. As the point of interest changes, the area to be encompassed can be displayed based on the underlying reduced contour information. When the researcher is satisfied with the result the pointer is pressed to create the gate.

The features described enable more efficient representation of contour plots in addition to several new features for contour plots. The polygon structures representing the contour may be quickly generated while minimizing memory and other resource usage. The resulting data structures also allow efficient transfer to third party applications. These data structures may also be used to include density information which is included contour information with plots that do not include density information such as a dot-plot.

Using contour and density plots can be made much for efficient by using the new features discussed. On-demand statistics, a hybrid contour-dot-plot and contour gating on dot-plots are just three possible implementations which may alone or in combination be used to allow the user to understand the data quickly so that user can make better decisions faster. On-demand statistics show exactly how much data resides at the contours. The hybrid contour-dot-plot allows a conventional dot-plot visual with density coloring while still providing the same statistics. With the contour gating, gates can be drawn quickly and accurately resulting in better classification.

Furthermore, the systems and methods described allow the event data to be compressed to reduce the number of points needed to represent polygon contours for the event data. Selection of a level within the contour can cause the generation of a gate. This allows limited resource devices, such as touchscreen wireless devices, to render and gate flow cytometry data in a resource efficient manner.

FIG. 17 shows examples of compatible locations for combining tiles. The candidate search locations shown in FIG. 17 assume a left to right and top to bottom tile scanning pattern. Accordingly, the candidate combination for the tile shown in the first row, first column of FIG. 17 is the tile to the left of the tile as the tile may be continuation of a polygon started in a previously scanned (and possible combined) tile. The candidate combination for the tile shown in the first row, column four indicates the start of a new polygon. Because the scanning pattern in the implementations shown in left to right and top to bottom, the tile shown in the first row, column four of FIG. 17 represents an upper corner of a new polygon.

As used herein, the terms "determine" or "determining" encompass a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, the terms "provide" or "providing" encompass a wide variety of actions. For example, "providing" may include storing a value in a location for subsequent retrieval, transmitting a value directly to the recipient, transmitting or storing a reference to a value, and the like. "Providing" may also include encoding, decoding, encrypting, decrypting, validating, verifying, and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may be implemented in hardware, software, firmware, or any combination thereof. Such techniques may be implemented in any of a variety of devices such as general purposes computers, wireless communication devices, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable medium may be a non-transitory storage medium. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding, or incorporated in a combined video encoder-decoder (CODEC).

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Various embodiments of the invention have been described. These and other embodiments are within the scope of the following claims.

What is claimed is:

1. A computer-implemented method of generating a gate for flow cytometry events from data for the flow cytometry events, the method comprising:
    under control of one or more processors,
        receiving data for flow cytometry events;
        generating a number of density levels to represent in a contour diagram, wherein the number of density levels is based at least in part on a density of the data, a number of events represented by the data, a number of parameters for each event represented by the data, or an analysis to be performed using the contour diagram;
        generating an initial contour diagram, wherein the initial contour diagram is defined by a plurality of polygons, said plurality of polygons representing regions corresponding to respective ones of the density levels in two dimensions, and wherein each polygon is defined as all or a portion of one of a plurality of tiles that divide the initial contour diagram in two dimensions;
        for a given tile included in the plurality of tiles of the initial contour diagram corresponding to one of the density levels, identifying an adjacent tile to the given tile at the one of the density levels that defines a first polygon matching a second polygon defined by the given tile based at least in part on a tile code for the given tile, wherein the tile code comprises a set of elements, each element encoding a density level for a point defining the second polygon;

when the adjacent tile is identified, combining the first polygon and the second polygon into a larger polygon, thereby reducing the number of polygons to form a reduced contour diagram defined by less data than the data for the initial contour diagram;

storing, in a memory, the reduced contour diagram;

receiving a message identifying a density level included in the density levels represented in the reduced contour diagram; and causing display of the reduced contour diagram for the identified density level, wherein the reduced contour diagram includes the gate identifying a group of flow cytometry events at the identified density level.

2. The computer-implemented method of claim 1, wherein generating the initial contour diagram comprises:
receiving a set of data;
generating a histogram for the set of data; and
generating the initial contour diagram based on the generated histogram.

3. The computer-implemented method of claim 1, wherein causing display of the reduced contour diagram comprises:
determining that the reduced contour diagram for the density level is stored in the memory; and
transmitting points defining the larger polygon to a device on which the reduced contour diagram will be displayed.

4. The computer-implemented method of claim 1, wherein the initial contour diagram includes one or more levels generated based on at least one of a probability density, a linear density, or a logarithmic density.

5. The computer-implemented method of claim 1, wherein each tile included in the plurality of tiles includes four corner points, and wherein a tile code is assigned for respective tiles, wherein the set of elements for the tile code comprises four elements, each element corresponding to one corner point of the tile.

6. The computer-implemented method of claim 5, wherein a value for a portion of the tile code is set based on a comparison of a corner point value and a contour level.

7. The computer-implemented method of claim 6, wherein identifying an adjacent tile is based on the tile code for the given tile and a tile scanning direction.

8. The computer-implemented method of claim 1, further comprising generating level information for a density level represented in the initial contour diagram, wherein the level information includes one or more of a level identifier, a number of events included within the density level, a percentage of total events included in the density level, a total number of events, a descriptive label for uniquely identifying the density level, and a visual cue for the density level.

9. The computer-implemented method of claim 1, further comprising transmitting the gate to a touch screen device.

10. An apparatus for generating a gate for particle analyzer events from data defining a contour diagram for the particle analyzer events, the apparatus comprising:
a processor configured to:
receive data for particle analyzer events;
generate a number of density levels to represent in a contour diagram, wherein the number of density levels is based at least in part on a density of the data, a number of events represented by the data, a number of parameters for each event represented by the data, or an analysis to be performed using the contour diagram;
generate an initial contour diagram, wherein the initial contour diagram is defined by a plurality of polygons, the plurality of polygons representing regions corresponding to respective ones of the density levels in two dimensions, and wherein each polygon is defined as all or a portion of one of a plurality of tiles that divide the initial contour diagram in two dimensions;
a contour reduction unit configured to:
for a given tile included in the plurality of tiles of the initial contour diagram corresponding to one of the density levels, identify an adjacent tile to the given tile at the one of the density levels that defines a first polygon matching a second polygon defined by the given tile based at least in part on a tile code for the given tile, wherein the tile code comprises a set of elements, each element encoding a density level for a point defining the second polygon;
when the adjacent tile is identified, combine the first polygon and the second polygon into a larger polygon, thereby reducing the number of polygons, to form a reduced contour diagram defined by less data than the data for the initial contour diagram; and
storing, in a memory, the reduced contour diagram;
a receiver configured to receive a message identifying a density level included in the density levels represented in the reduced contour diagram, wherein the processor is further configured to cause display of the reduced contour diagram for the identified density level, wherein the reduced contour diagram includes the gate identifying a group of particle analyzer events at the identified density level.

11. The apparatus of claim 10, further comprising:
a receiver configured to receive a set of data;
a histogram generator configured to generate a histogram for the set of data; and
a contour generator configured to generate the initial contour diagram based on the generated histogram.

12. The apparatus of claim 10, wherein the receiver is further configured to receive the data for the particle analyzer events via a communication channel connecting the apparatus with the particle analyzer.

13. The apparatus of claim 10, wherein the initial contour diagram includes one or more levels generated based on at least one of a probability density, a linear density, or a logarithmic density.

14. The apparatus of claim 10, wherein each tile included in the plurality of tiles includes four corner points, and wherein a tile code is assigned for respective tiles, wherein the set of elements for the tile code comprises four elements, each element corresponding to one corner point of the tile.

15. The apparatus of claim 14, wherein a value for a portion of the tile code is set based on a comparison of a corner point value and a contour level.

16. The apparatus of claim 15, wherein identifying an adjacent tile is based on the tile code for the given tile and a tile scanning direction.

17. The apparatus of claim 10, wherein the processor is further configured to generate level information for a density level represented in the initial contour diagram, wherein the level information includes one or more of a level identifier, a number of events included within the density level, a percentage of total events included in the density level, a total number of events, a descriptive label for uniquely identifying the density level, and a visual cue for the density level.

18. The apparatus of claim 10, further comprising a transmitter configured to transmit the gate to a touch screen device.

19. The apparatus of claim 18, wherein the receiver is configured to receive the message including an identifier for a level of the contour from the touch screen device.

20. A non-transitory computer-readable storage medium comprising instructions executable by a processor of an apparatus for generating a gate for particle analyzer events from data defining a contour diagram for the particle analyzer events, the instructions causing the apparatus to:

receive data for particle analyzer events;

generate a number of density levels to represent in a contour diagram, wherein the number of density levels is based at least in part on a density of the data, a number of events represented by the data, a number of parameters for each event represented by the data, or an analysis to be performed using the contour diagram;

generate an initial contour diagram, wherein the initial contour diagram is defined by a plurality of polygons, said plurality of polygons representing regions corresponding to respective ones of the density levels in two dimensions, and wherein each polygon is defined as all or a portion of one of a plurality of tiles that divide the initial contour diagram in two dimensions;

for a given tile included in the plurality of tiles of the initial contour diagram corresponding to one of the density levels, identify an adjacent tile to the given tile at the one of the density levels that defines a first polygon matching a second polygon defined by the given tile based at least in part on a tile code for the given tile, wherein the tile code comprises a set of elements, each element encoding a density level for a point defining the second polygon;

when the adjacent tile is identified, combine the first polygon and the second polygon into a larger polygon, thereby reducing the number of polygons, to form a reduced contour diagram defined by less data than the data for the initial contour diagram;

store, in a memory, the reduced contour diagram;

receive a message identifying a density level included in the density levels represented in the reduced contour diagram; and cause display of the reduced contour diagram for the identified density level, wherein the reduced contour diagram includes the gate identifying a group of particle analyzer events at the identified density level.

* * * * *